(12) United States Patent
Auerbach et al.

(10) Patent No.: US 12,251,499 B2
(45) Date of Patent: Mar. 18, 2025

(54) SYRINGE INCLUDING DIFFERENT MATERIALS

(71) Applicant: SCHOTT Pharma Schweiz AG, St. Gallen (CH)

(72) Inventors: Judith Auerbach, Niederteufen (CH); Bastian Fischer, St. Gallen (CH); Helena Derksen, St. Gallen (CH)

(73) Assignee: SCHOTT Pharma Schweiz AG, St. Gallen (CH)

( * ) Notice: Subject to any disclaimer, the term of this patent is extended or adjusted under 35 U.S.C. 154(b) by 148 days.

(21) Appl. No.: 17/954,750

(22) Filed: Sep. 28, 2022

(65) Prior Publication Data

US 2023/0019725 A1 Jan. 19, 2023

Related U.S. Application Data

(63) Continuation of application No. 15/860,285, filed on Jan. 2, 2018, now abandoned.

(30) Foreign Application Priority Data

Jan. 2, 2017 (DE) ...................... 10 2017 200 007.4

(51) Int. Cl.
*A61L 31/04* (2006.01)
*A61L 31/06* (2006.01)
(Continued)

(52) U.S. Cl.
CPC ............. *A61L 31/048* (2013.01); *A61L 31/06* (2013.01); *A61M 5/3134* (2013.01); *A61M 5/34* (2013.01); *A61M 5/344* (2013.01); *A61M 5/345* (2013.01); *A61M 5/346* (2013.01); *A61M 5/347* (2013.01); *B29C 45/0001* (2013.01); *B29C 45/164* (2013.01); *B29C 45/1676* (2013.01); *B29C 65/08* (2013.01); *B29C 65/565* (2013.01); *B29C 66/712* (2013.01); *B29C 66/72* (2013.01); *B29C 66/73152* (2013.01); *A61M 2207/00* (2013.01); *B29K 2023/06* (2013.01);
(Continued)

(58) Field of Classification Search
CPC ... A61L 31/048; A61M 5/344; A61M 5/3134; A61M 5/34; A61M 5/345; A61M 2205/02
See application file for complete search history.

(56) References Cited

U.S. PATENT DOCUMENTS

| 4,220,151 A | 9/1980 | Whitney |
| 6,027,482 A | 2/2000 | Imbert |

(Continued)

FOREIGN PATENT DOCUMENTS

| DE | 692 26 166 T2 | 12/1998 |
| DE | 202 15 807 U1 | 2/2003 |

(Continued)

*Primary Examiner* — Bradley J Osinski
(74) *Attorney, Agent, or Firm* — TAYLOR & EDELSTEIN

(57) ABSTRACT

A syringe includes a syringe body, a syringe cone having a distal opening, and a connection arranged in the region of the syringe cone, wherein the syringe body includes a first material and the connection includes a second material, and wherein the first material is different from the second material and the second material is a softer material than the first material.

8 Claims, 12 Drawing Sheets

(51) Int. Cl.
*A61M 5/31* (2006.01)
*A61M 5/34* (2006.01)
*B29C 45/00* (2006.01)
*B29C 45/16* (2006.01)
*B29C 65/00* (2006.01)
*B29C 65/08* (2006.01)
*B29C 65/56* (2006.01)
*B29K 23/00* (2006.01)
*B29L 31/00* (2006.01)

(52) U.S. Cl.
CPC ...... *B29K 2023/08* (2013.01); *B29K 2023/12* (2013.01); *B29K 2023/38* (2013.01); *B29K 2995/007* (2013.01); *B29K 2995/0089* (2013.01); *B29L 2031/7544* (2013.01)

(56) References Cited

U.S. PATENT DOCUMENTS

| | | | |
|---|---|---|---|
| 6,074,373 A | 6/2000 | Sudo et al. | |
| 6,221,046 B1 * | 4/2001 | Burroughs | A61M 5/31551 604/207 |
| 8,038,182 B2 | 10/2011 | Kurimoto et al. | |
| 10,098,812 B2 | 10/2018 | Kücük et al. | |
| 2006/0106349 A1 | 5/2006 | Kito et al. | |
| 2012/0157928 A1 | 6/2012 | Mermet | |
| 2013/0079276 A1 | 3/2013 | Van Goudoever et al. | |
| 2013/0231274 A1 | 9/2013 | Lee et al. | |
| 2013/0338603 A1 | 12/2013 | Roedle et al. | |
| 2014/0025017 A1 | 1/2014 | Horita et al. | |
| 2014/0358078 A1 | 12/2014 | Fischer et al. | |
| 2016/0206821 A1 | 7/2016 | Horiuchi et al. | |

FOREIGN PATENT DOCUMENTS

| | | |
|---|---|---|
| EP | 0 838 229 A2 | 4/1998 |
| EP | 1 080 742 A1 | 3/1999 |
| EP | 1 410 819 A1 | 4/2004 |
| EP | 1 923 086 A1 | 5/2008 |
| EP | 3 042 689 A1 | 7/2016 |
| JP | 2006-166961 A | 6/2006 |
| JP | 2008-246070 A | 10/2008 |
| JP | 2015-228878 A | 12/2015 |
| WO | 2008/156036 A1 | 12/2008 |
| WO | 2012/116790 A1 | 9/2012 |

* cited by examiner

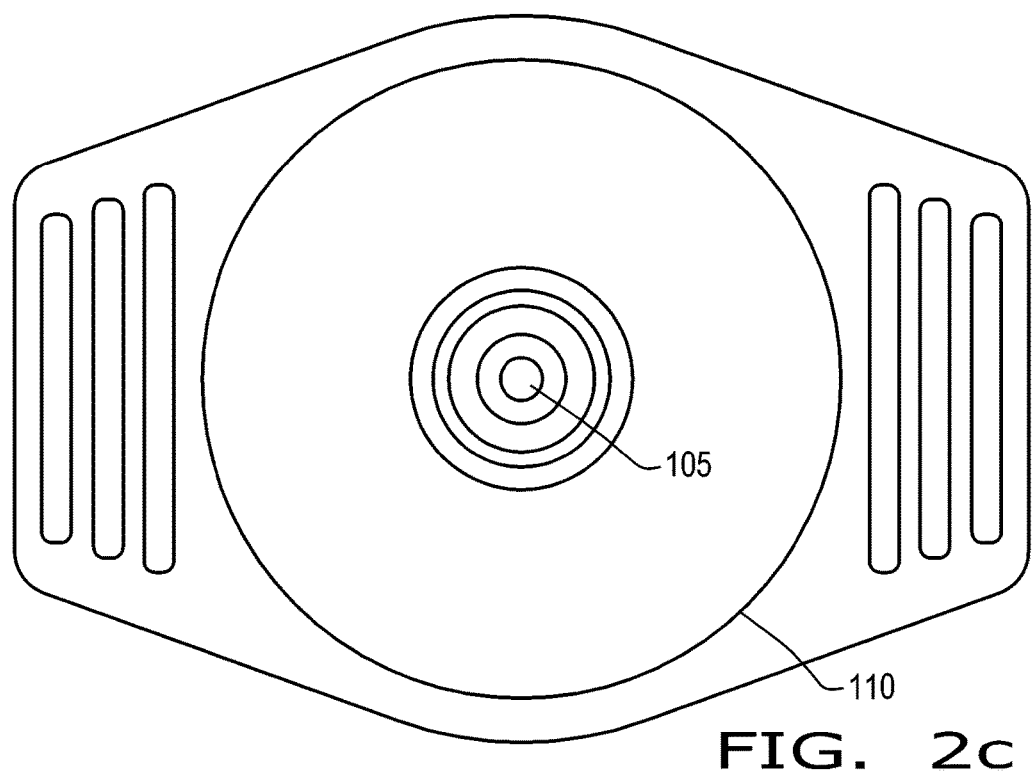
FIG. 2c
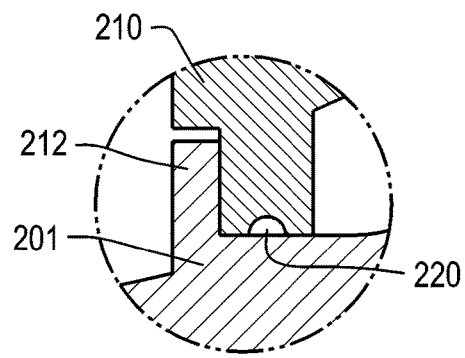
FIG. 3a.2
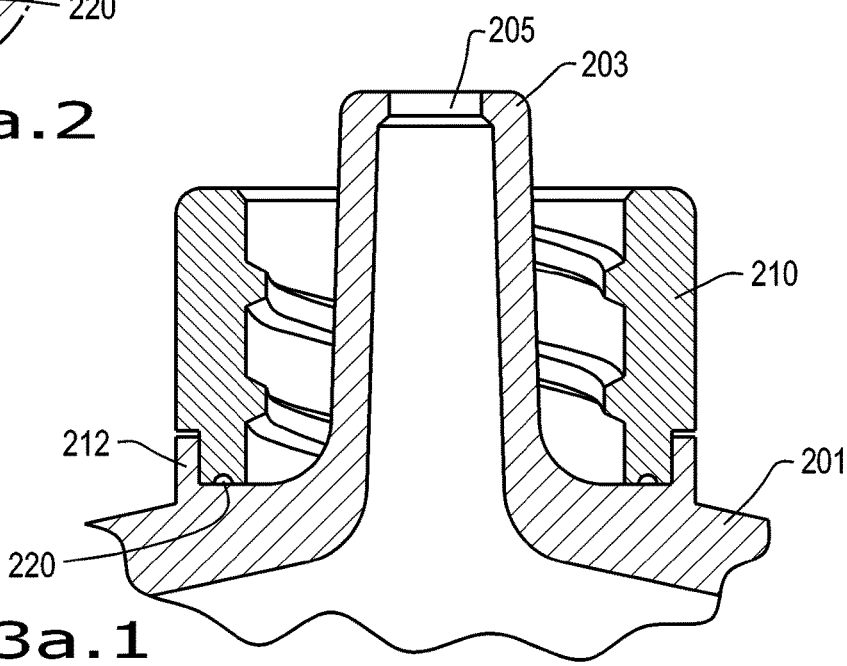
FIG. 3a.1

SYRINGE INCLUDING DIFFERENT MATERIALS

CROSS REFERENCE TO RELATED APPLICATIONS

This is a continuation of U.S. patent application Ser. No. 15/860,285, entitled "SYRINGE INCLUDING DIFFERENT MATERIALS", filed Jan. 2, 2018, which is incorporated herein by reference.

BACKGROUND OF THE INVENTION

1. Field of the Invention

The invention relates to syringes, and in particular, syringes having a syringe body, a syringe cone including a distal opening, and a connection arranged in the region of the syringe cone.

2. Description of the Related Art

Syringes have become known from a multitude of patents that have a connection for various connectors that are mounted manually onto the tip of the syringe.

A syringe of this type is described, for example in US 2013/079 276 A. A syringe body has become known from US 2013/079 276 A wherein a transport cap, an intravenous port or an injection needle can be screwed into a thread above the syringe cone. If, for example a transport cap is screwed into the thread, the syringe cone can be protected.

A syringe with a thread in the region of the Luer-Lock connection has become known from DE 202 158 07 U1, wherein the thread is part of the syringe body. The Luer-Lock connection according to DE 202 158 07 U1 has an internal thread in the region of the syringe cone.

DE 692 26 166 T2 also describes a plastic syringe, wherein the needle connecting piece is in the embodiment of a standard Luer-Lock connection with a Luer cone and an outside wall with a screw thread about its inside circumferential wall.

A similar arrangement has also become known from EP 1 080 742 A1 or EP 1 410 819 A1. In both, EP 1 080 742 A1 and EP 1 410 819 A1 the thread that serves as the connection for connectors, is a part of the Luer cone. Similar systems wherein parts of the Luer cone are provided with an inside thread providing the connection for connectors, or respectively syringe needles, etc. are described in EP 1 923 086 A1 and EP 3 042 689 A1.

From WO 2012/116 790 A1 a syringe has become known, with a syringe cylinder and a needle attachment piece that is provided at a distal end of the syringe cylinder, wherein the syringe features a closure that includes a closure cap that closes the needle attachment piece in a sealing manner, and a safety cap, wherein the safety cap surrounds the closure cap and is secured via a retaining ring on the needle attachment piece. The syringe is characterized in that at least the safety cap and the closure cap are a single component.

Mention is made in WO 2012/116 790 A1 that the retaining ring, as well as the closure cap and the safety ring can be manufactured from a thermoplastic elastomer (TPE) or polypropylene. On the other hand, the needle attachment piece preferably includes glass, or consists of glass. An embodiment of the needle attachment piece and the syringe that consists of hard plastic material including cycloolefin-copolymer (COC) or cycloolefin-polymer (COP) is not described in WO 2012/116 790 A1.

When using COC or COP as the material for the syringe cylinder, the problem arises that due to mechanical stresses between the connection or respectively the thread and the mating thread that is allocated to the connector, cracks can occur in the material of the syringe body, thereby compromising the functionality of the syringe. In the worst-case scenario such mechanical stresses result in damage of the syringe itself or in leakage of same. This is the case for instance, if COC (cycloolefin-copolymer) or COP (cycloolefin-polymer) are selected as the material for the syringe body.

However, U.S. Pat. No. 8,038,182 B1 and EP 0 838 229 A2 also describe syringe bodies consisting of COC. To avoid damage to the syringe body consisting of COC, U.S. Pat. No. 8,038,182 B1 suggests an expensive design of the connection that is introduced into the thread of the Luer-Lock, wherein upward and downward directed forces in the connecting thread result in that the connection expands into a free space, and radial forces acting upon the syringe body that could lead to a break, are avoided. In EP 0 838 229 A2 a break is avoided through the use of a retaining element.

In all arrangements according to the current state of the art it was disadvantageous that the connecting piece, for example the thread of the Luer-Lock was of the same material as the syringe itself. This resulted in that, due to mechanical stresses between the connection or respectively the thread and the mating thread that is allocated to the connector, cracks occurred in the material of the syringe body, thereby compromising the functionality of the syringe. In the worst-case scenario such mechanical stresses can result in damage of the syringe itself or in leakage of same. This was the case in particular if the material of the syringe body was for example COC (cycloolefin-copolymer) or COP (cycloolefin-polymer) and the connectors consisted of another material such as PC (polycarbonate), PVC (polyvinyl chloride), PE (polyethylene) or PA (polyamide).

If—in order to avoid the problem of cracking—the entire syringe body consists of a softer plastic material, the problem arises that on the one hand a polypropylene (PP) syringe body due to its material properties can indeed compensate for the stresses caused by the connectors; however, a pharmaceutical medium cannot be stored over several months in a polypropylene (PP) syringe body due to the diffusion characteristics.

An additional problem consists in that connectors that, for example are to be screwed into the thread of the Luer-Lock include a multitude of different materials such as PC, PVC, polyethylene (PE) that will connect with the material of the Luer-Lock thread. An additional problem of the current connectors is that they are generally screwed manually into the thread and that the insertion torque can fluctuate over a wide range, for example 12 Ncm to 56 Ncm, preferably 12 Ncm to 80 Ncm. These stresses result in cracks on either the thread or on the connector. At worst, breaks can even occur due to these stresses.

What is needed in the art is a syringe and method of manufacturing a syringe that overcomes the disadvantages of the current state of the art.

SUMMARY OF THE INVENTION

According to an aspect of the invention, there is provided a syringe having a syringe body with a syringe cone that comprises a distal opening and a connection that is arranged in the region of the syringe cone, the materials of connection and syringe body are different. The syringe body consists of a first material and the connection, in particular the thread consists at least in sections of a second material. According to an aspect of invention the second material is a softer material than the first material. The second material can for example be a thermoplastic elastomer (TPE), an elastomer or polypropylene (PP), polycarbonate (PC), polyethylene (PE), polyamide (PA) or COC-E, that is characterized in that it has a higher impact strength and/or a lower E-module. The second soft material is preferably used where great forces occur when screwing connectors into the connection. A sectional arrangement is also possible in locations of high forces.

In the current invention a soft material is understood to be a material whose E-module is by 10 to 60% lower than that of the hard material. The E-module of the first hard material is preferably in the range of greater than 2500 to 3500 MPa, preferably 2700 to 3200 MPa and that of the softer second material in the range of 1200 to 2500 MPa, preferably 1500 to 1800 MPa.

The second material is moreover characterized by a high impact strength of greater than 2 $kJm^2$.

Impact strength is understood to be a measure for the resistance of a material relative to a sudden dynamic stress. The measure is the performed impact strength relative to the fractured surface, expressed in Joule per surface area $[J/cm^2]$. Soft materials generally have a high impact strength, whereas in contrast hard materials are materials with low impact strength. Brittle materials such as COC have an impact strength of less than 2 $kJ/m^2$.

Due to the fact that in the connecting region, particularly in the region of the thread, a softer material is used than for the syringe body itself, it is possible that the softer material absorbs stresses and load peaks that can occur when screwing a connector or adaptor into the thread and that these are then not transferred to the syringe body. By use of a soft plastic material it is possible to compensate for various stress situations, for example load peaks, torques, etc. The geometry of the connection is preferably the same as that of the Luer-Lock adapter (LLA). This ensures that a standard syringe is provided that can interact with diverse connecting elements, in particular with connectors and adaptors.

The softer material in the region of the connection, in particular the thread can however not prevent the occurrence of mechanical stresses. The softer material does however provide a buffer to absorb load peaks, for example when screwing in the connector and to distribute these evenly across the syringe body. The softer material thus represents a kind of buffer. It is possible that the soft material represents the thread geometry, as well as being introduced as a buffer between the thread of the connector and the thread of the syringe body that serves as the connection.

The first, hard material of the syringe body is preferably a COC (cycloolefin-copolymer) or COP (cycloolefin-polymer). The advantage in using the cycloolefin-copolymer or cycloolefin-polymer is, that these materials provide an effective water vapor barrier that makes it possible to store liquids, in particular liquid medicines over longer time periods which may be several years, without or respectively with only very low volume loss.

The inventors have found that when using COC and COP as materials for the syringe body, the problem of crack formation can be prevented if the connection for the connectors or the Luer-Lock is manufactured from a softer material than the syringe body. By using a softer material, it becomes possible that even with high insertion torques, stresses at the thread or the connector and thus breaks, due to these stresses in the syringe, can be avoided.

An elastomer, especially a thermoplastic elastomer (TPE) or COC-E is preferably used as a softer second material. Other possible polymers are polypropylene (PP), polyethylene (PE), polycarbonate (PC), polyamide (PA).

To be able to use the syringe for pharmaceutical products it is necessary that the first, as well as also the second material of the syringe body or the connection includes materials which can be sterilized at temperatures >100° C., especially 121° C., in particular at a maximum of 180° C. Examples of such materials for the syringe body are COC or COP and for the connector COC-E, TPE, PP, PE, PC or PA.

It is especially preferred if the syringe body represents a first component of the syringe and the connection, in particular the thread and possibly also the cone represent a second component. First and second component are separate components which must be connected with each other, for example by means of welding. The connection of first and second component can however also occur in a different manner. A mechanical and/or a coalesced and/or a friction type and/or a form fitting connection would be conceivable.

It is especially preferred if the connection between syringe body and connection is arranged such, that the first component is indeed connected with the second component, that however this connection can be detached at a predetermined force, in other words if the first component is definably detachably connected with the second component. In such an arrangement a visible break is initiated in an overload situation at a defined location instead of at a critical location, for example at a sealing point that is not visible.

In the manufacture of a syringe according to the invention, various possibilities are conceivable. A first method is characterized in that the syringe body consists of a first material and the connection, especially the thread consists of a second material, wherein the second material is softer than the first material, and first and second materials are provided separately. In a further procedural step, the connection and the syringe body are connected with each other through material fit and/or friction fit and/or form fit and/or coalesced fit. In the case of a coalesced fit it is especially preferred when the syringe body and connection are connected with each other through welding, in particular ultrasonic welding.

Alternatively, to the previously discussed manufacturing method wherein each component is produced individually it is also possible to produce the entire component, in other words the syringe with syringe body and connection by means of multicomponent injection molding. In the multicomponent injection molding process, an injection molded part is obtained that consists of two or more different plastics. Different methods are conceivable in the multicomponent injection molding process. An injection molding machine for multicomponent injection molding includes two or more injection units, but only one clamping unit. In addition, a pre-molded part can be inserted into a tool for over-molding. With multicomponent injection molding the relevant components can be produced cost effectively in only one work cycle. In addition, with multicomponent injection molding lower positional tolerances can be realized than with assembly.

With multicomponent injection molding it is possible that the soft material is sprayed onto the hard material, or vice versa. This saves the assembly step and results in a physical connection between the hard and soft material. With multicomponent injection molding it is possible that the attachment can be adjusted between the soft and the hard material, so that the connector is attached detachably on the syringe body.

It is especially preferred if the softer material has an increased coefficient of friction that ensures that the thread cannot be over-tightened. In connecting the first material to the second material the attachment surface should be designed such that an as large as possible surface contact of the two materials ensures the stability of the connection.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIGS. 2a-2c is a second version of a mechanical attachment of the connector on the syringe body;

FIGS. 3a1-3c is a version with syringe body and connector as individual parts, wherein he individual parts are connected with one another by means of ultrasonic welding;

Corresponding reference characters indicate corresponding parts throughout the several views. The exemplifications set out herein illustrate embodiments of the invention, and such exemplifications are not to be construed as limiting the scope of the invention in any manner.

DETAILED DESCRIPTION OF THE INVENTION

Figure 1A:
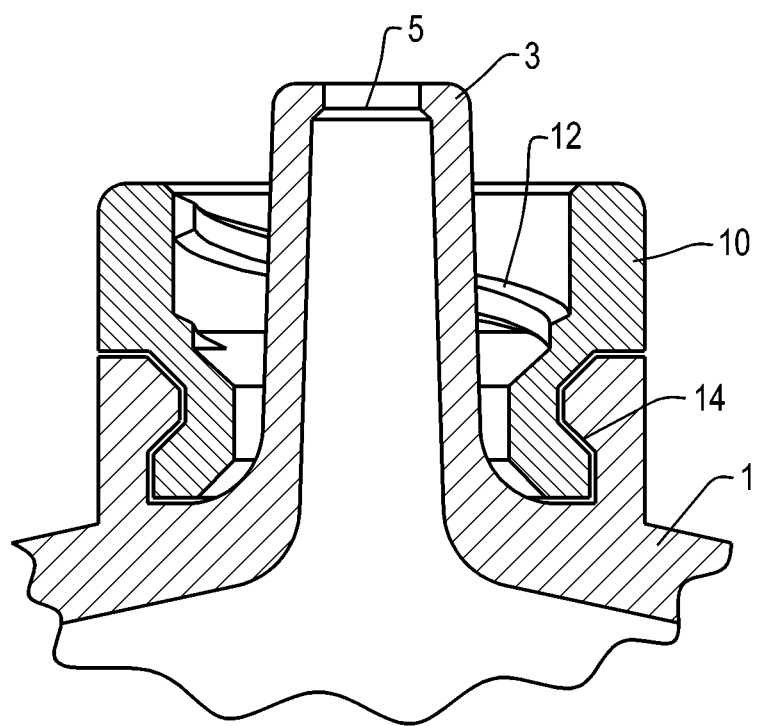
FIGS. 1a-1c is a first version of a mechanical attachment of the connector on the syringe body.
Figure 1B:
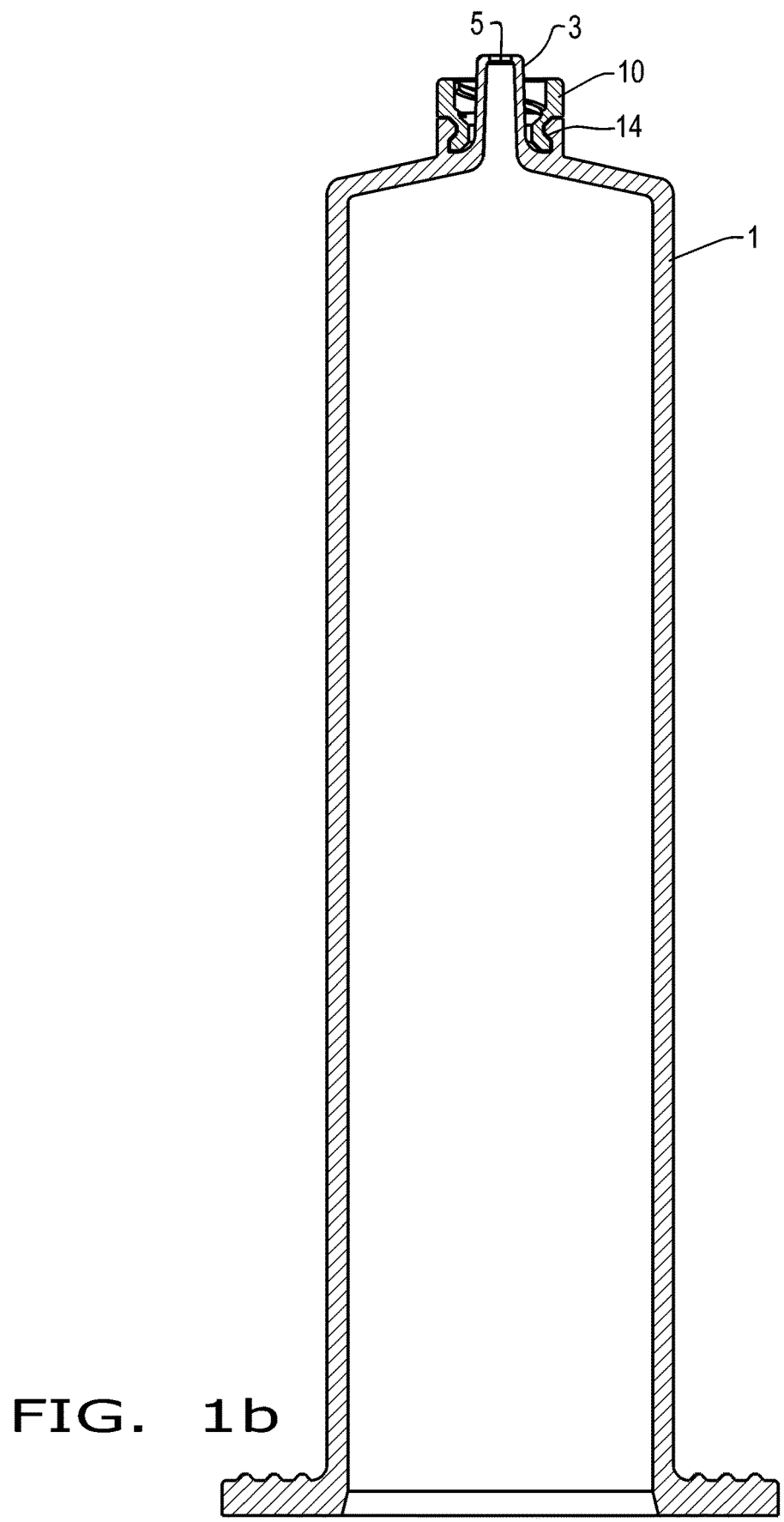
Figure 1C:
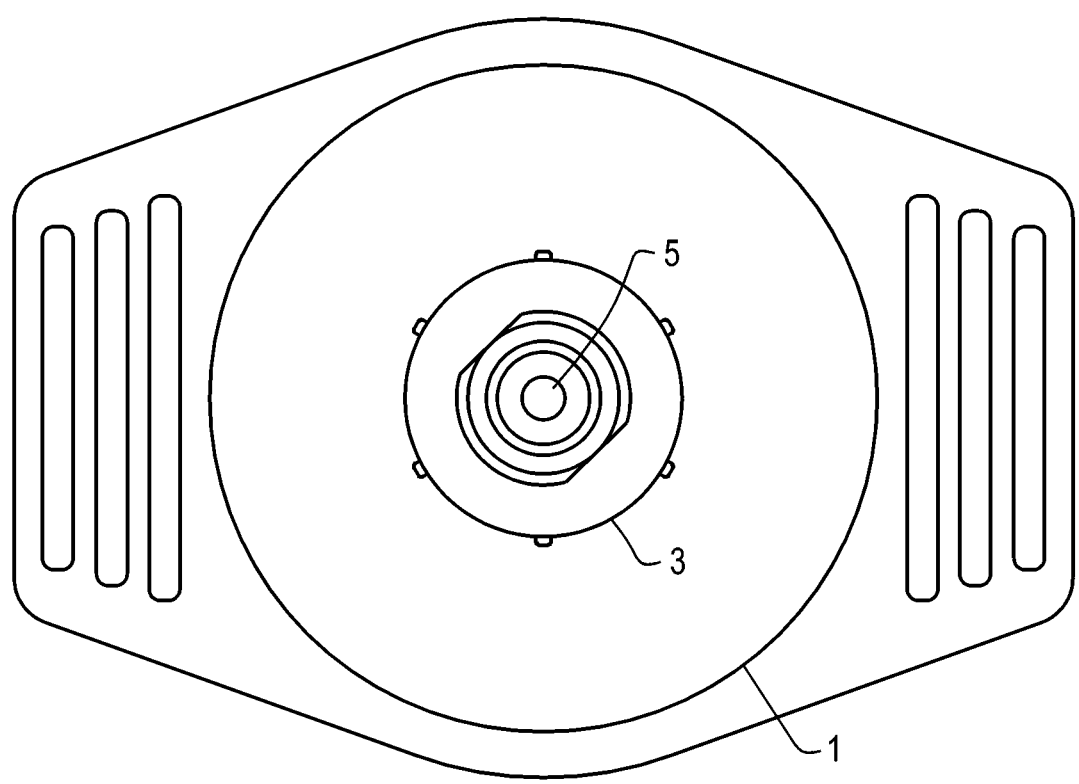

Referring now to the drawings, and more particularly to FIG. 1, there is shown a syringe body 1 which generally includes a syringe cone 3, with a distal opening 5. Of entire syringe body 1, only the upper part of the syringe in the region of syringe cone 3 is shown. Syringe body 1 preferably consists of a hard plastic, for example a cycloolefin-copolymer (COC) or cycloolefin-polymer (COP). A connector 10 for connectors or respectively attachment of syringes is arranged about syringe cone 3. Connection 10 in this example is an attachment with an inside thread 12, without being limited to same. Connection 10 in this example is an independent part vis-à-vis syringe body 3. In the illustrated embodiments according to FIG. 1, the syringe body as the first component and the connector as the second component are only mechanically connected with one another. For example, connection 10 is placed onto the syringe body and is locked in place in an undercut 14, in other words, the connector is held in a form-fit. Separate component 10 can either be screwed into or pressed onto undercut 14. To more effectively hold component 10 on syringe body 1, overmolding may be provided in the region of the connection, for example with a plastic. Over molding stabilizes the connection of component 10 on the syringe body. According to the invention, the material of connection 10 is softer than the material of the syringe body. The E-module of the syringe body consisting of a hard material is preferably 2500-3500 MPa, the E-module of the connection consisting of a soft material 1200-2500 MPa. The module of the softer material of connection 10 is generally 10 to 60% lower than the E-module of the hard material of the syringe body. Whereas the material used for the syringe body is a cycloolefin-copolymer or cycloolefin-polymer, the soft material of the connection is a thermoplastic elastomer (TPE) or an elastomer or polypropylene (PP) or polyethylene (PE). A notched impact strength of more than 2 kJ/m$^2$ characterizes the specified soft materials. FIG. 1c is a top view of syringe body 1. Same components as in FIG. 1a-1b are identified with same reference numbers. Hard materials such as cycloolefin-copolymer (COC) or cycloolefin-polymer (COP) have a low notched impact strength of less than 2 kJ/m$^2$.

Figure 2A:
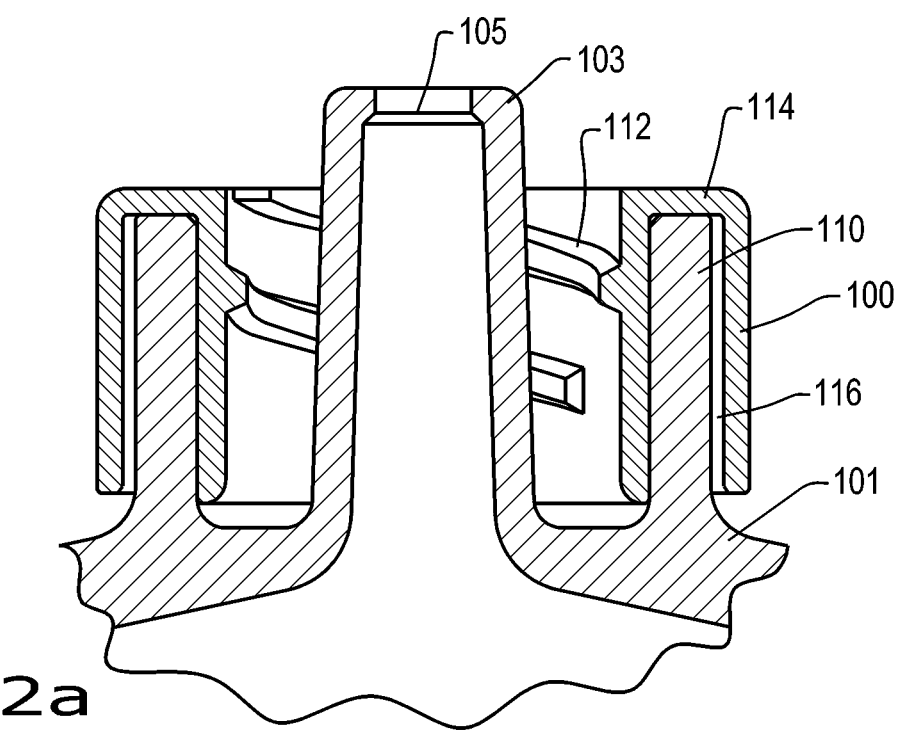
Figure 2B:
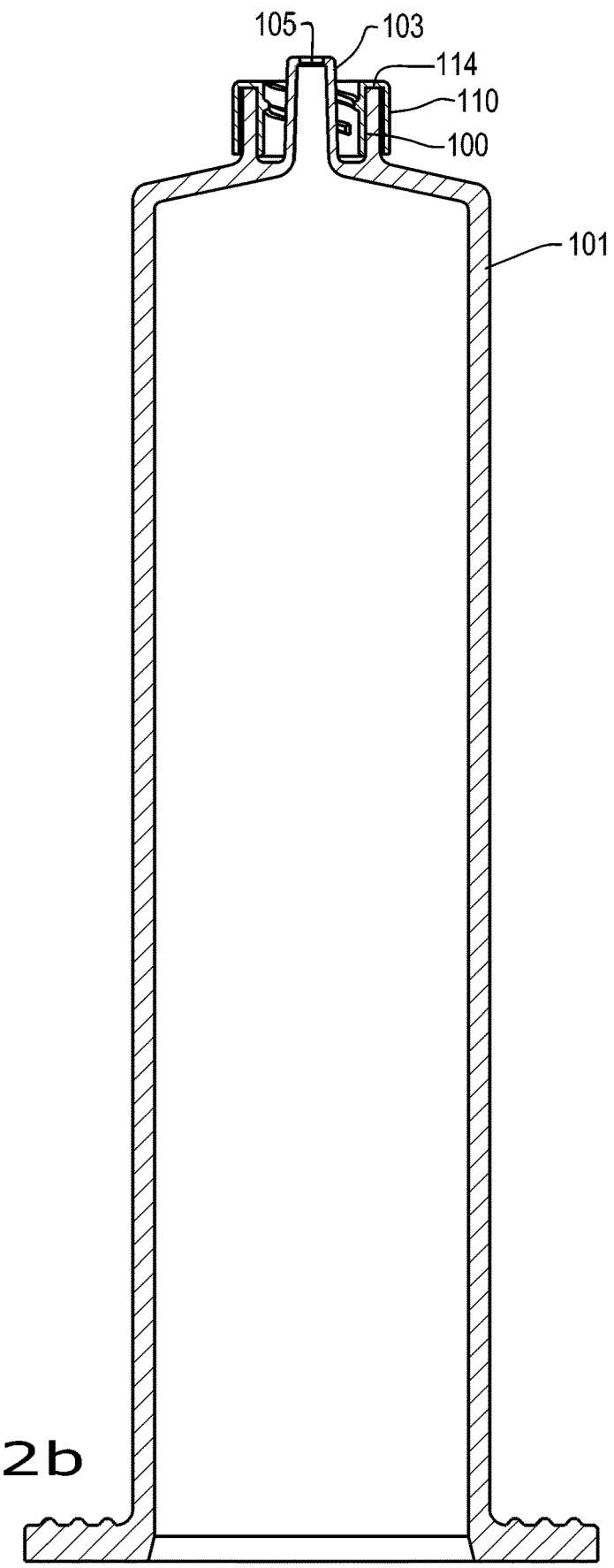

FIGS. 2a-2c illustrate an alternative embodiment of a mechanical union of a connection 100 on a syringe body 101. Herein, FIG. 2a depicts connecting piece 100 with inside thread 112. Connecting piece 100 consists of a softer material, for example a thermoplastic elastomer, an elastomer, polycarbonate, polypropylene or polyethylene, compared with the hard material of the syringe body which may consist of COC or COP. Connecting piece 100 is characterized in that, in addition to inside thread 112, it features a circumferential attachment 114 with a hollow space 116, wherein protrusions or elevations 110 of syringe body 101 can engage in hollow space 116. By pressing the connection, it can be held on syringe body 101 via hollow space 116. The detailed design of connecting piece 100 of the syringe body is shown in FIG. 2a. As shown in FIG. 2b, syringe body 101 consists of a hard material, for example COC and comprises a syringe cone 103 with a distal opening 105. In addition to syringe cone 103, syringe body 101 features a circumferential elevation 110. Hollow spaces 116 of connecting piece 100 engage into circumferential elevation 110 according to FIG. 2a and are held for example by pressing following the attachment of the connecting piece onto elevation 110. FIG. 2b illustrates a complete syringe body 101 with attached connecting piece 110. Same components as in FIG. 2 are identified by the same reference numbers. This applies also to the top view according to FIG. 2c.

FIGS. 3a1 to 3c illustrates the attachment of the connection with the syringe body by means of material fit, for example by means of welding. FIG. 3a1 shows a view of a syringe body 201 according to the invention, with a connecting piece 210 on syringe body 201. The syringe body in FIG. 3a is a plastic syringe consisting of a hard material, for example cycloolefin-copolymer (COC) or cycloolefin-polymer (COP). Syringe body 201 again includes a distal tip 203 with a distal opening 205. Connecting piece 210 is arranged around distal tip 203, with an inside thread 212 for screwing in of a connector. As in the previously described embodiments, connecting piece 210 consists of a softer material than syringe body 201, for example of polyethylene or polypropylene or COC-E. The softer material can also be used in sections. In that case it is preferably used in areas where high forces occur when screwing in the connectors.

Figure 3B:
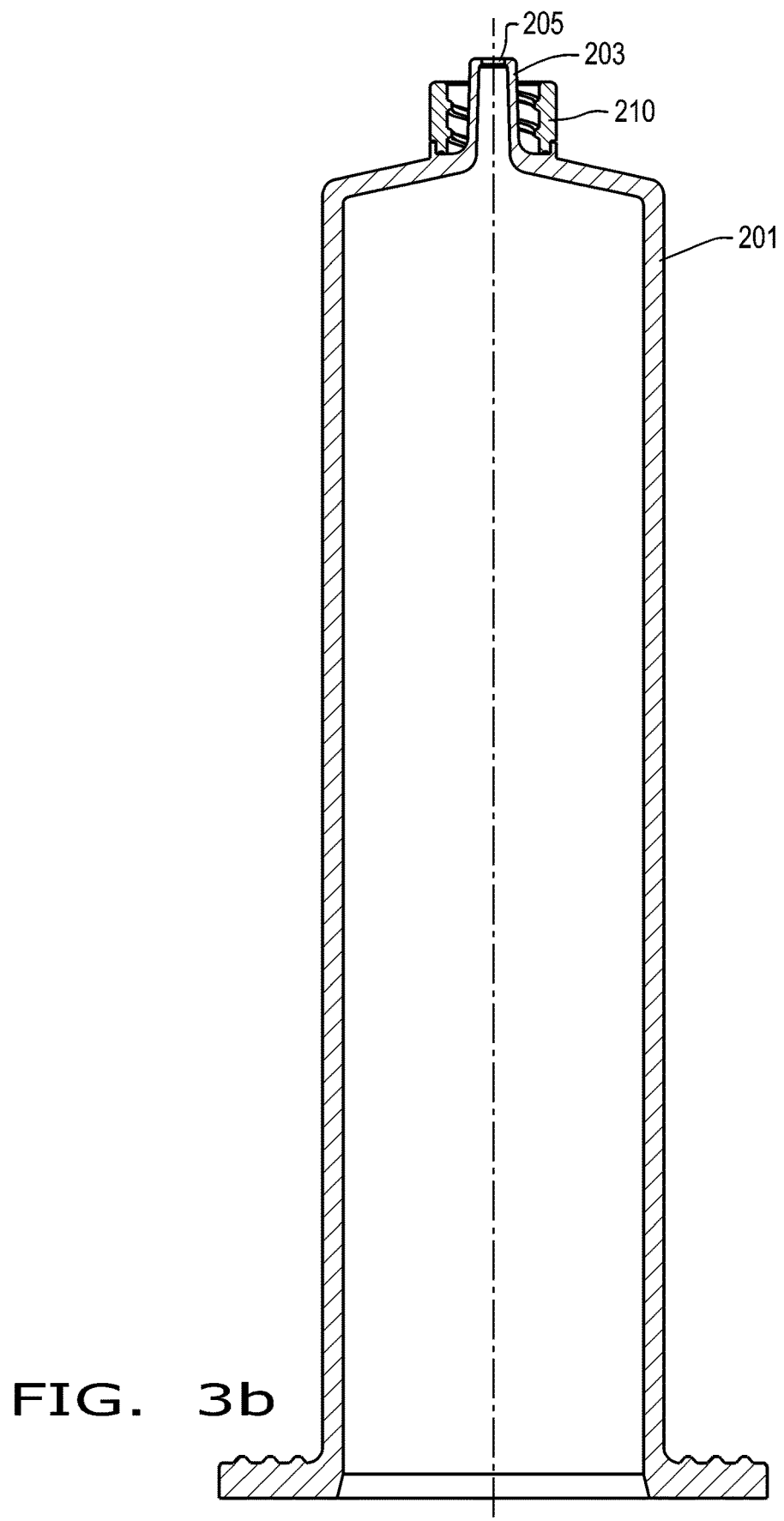
Figure 3C:
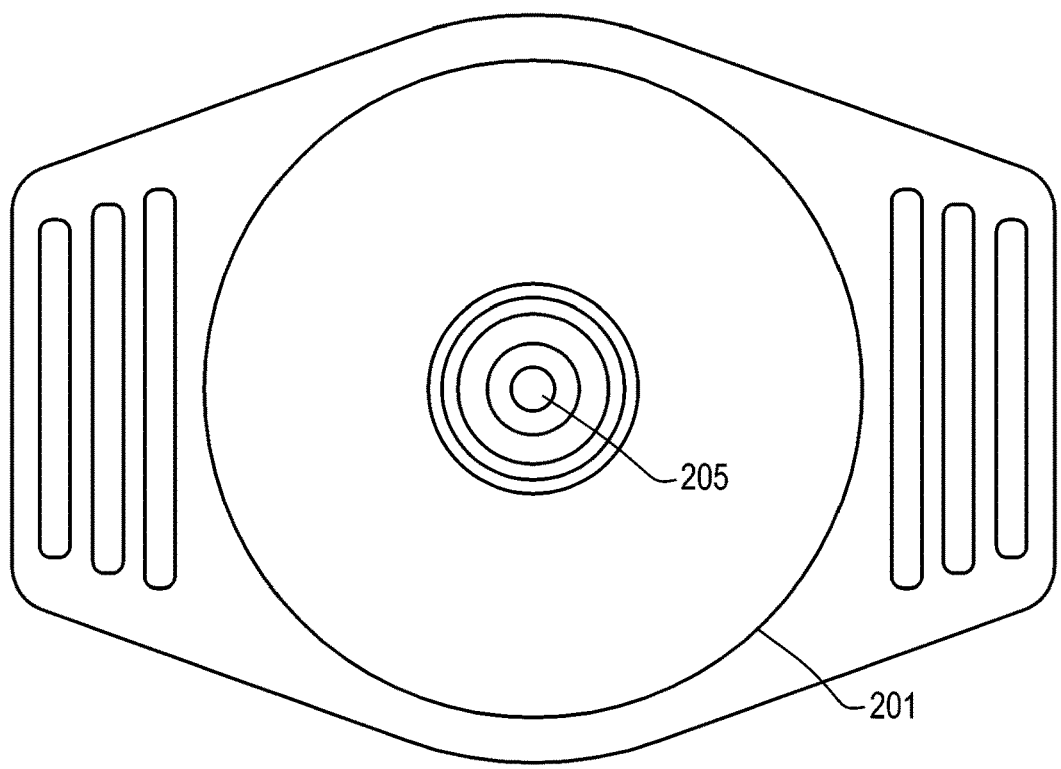

FIG. 3a2 details the area from FIG. 3a1 that shows the connection between separate connecting piece 210 and syringe body 201. This connection can occur selectively or over the complete support surface. Separate connecting piece 210 is located with protrusions 212 of the syringe body. After placing separate connecting piece 210 on the syringe body, connecting piece 210 is joined the syringe body through coalescent fit, in other words material bonding, for example by means of welding, in particular ultrasonic welding. For the purpose of ultrasonic welding, connecting piece 210 or syringe body 201 have material provisions 220, that—by means of a sonotrode—are caused to oscillate and thus to bond. The ultrasonic welding can occur selectively or across the surface. If material provisions 220 are used, the welding occurs selectively. In heated ultrasonic welding the selection of the materials, especially their combination is important. If there is too great a difference between the fusion points, bonding of the materials is no longer possible FIG. 3b again illustrates in detail the entire syringe body 201 with ultrasonically welded connecting piece 210. FIG. 3c is a top view of the design according to FIGS. 3a1-3a2. Same components are identified with the same reference numbers.

In an alternative arrangement of the invention, the complete syringe body with connecting piece can be produced by a multicomponent injection molding process, instead of bonding the connector with the syringe body by means of welding, in particular ultrasonic welding. This is shown in FIGS. 4a-4b for a first embodiment, and in FIGS. 5a-5d for a second embodiment.

Figure 4A:
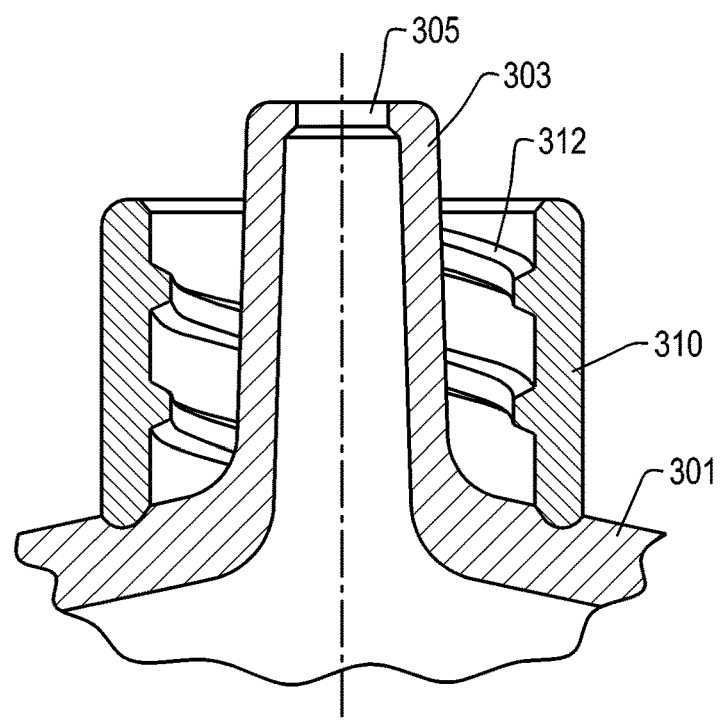
FIGS. 4a-4b is a first embodiment of a connector and syringe body created by means of multicomponent injection molding.

FIG. 4a illustrates syringe body 301, produced by multi-component-injection molding. Syringe body 301 includes again a connecting piece 310 in the region of syringe cone 303 with an inside thread 312, consisting of a softer material than syringe body 301. As stated previously, the softer material is characterized by an E-module.

Figure 4B:
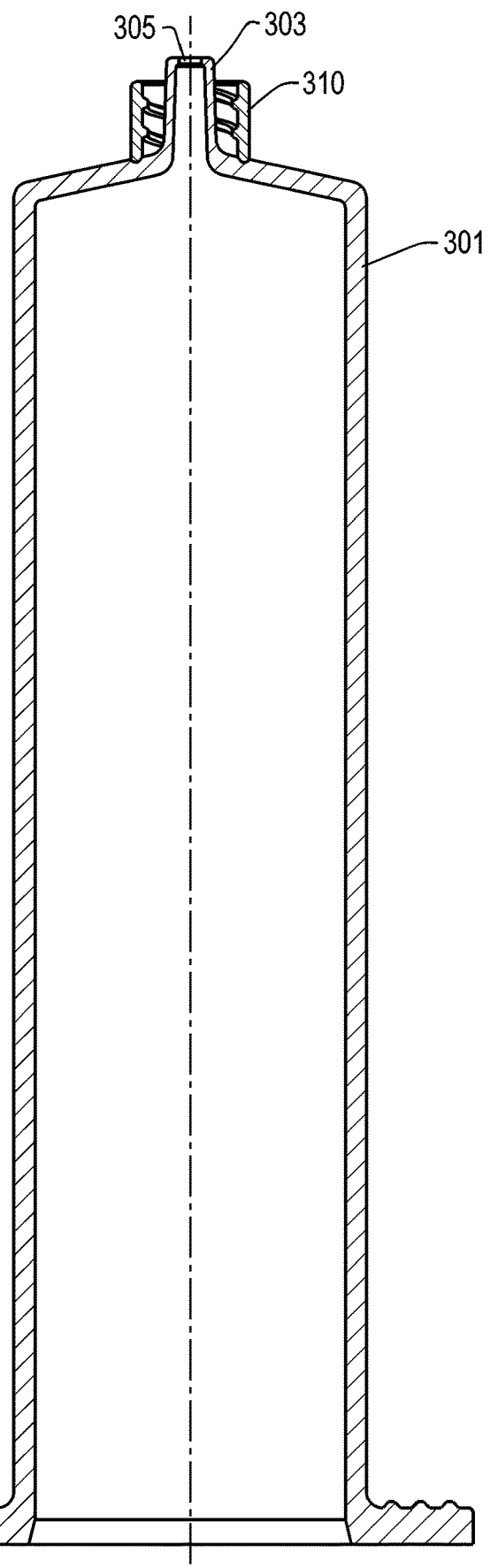

FIG. 4b is an overall view of the syringe from FIG. 4a. The material of syringe body 301 is a hard plastic material, for example COC or COP, whereas the material of connecting piece 310 is a soft material, for example polypropylene or polyethylene or COC-E. Also, clearly visible in FIG. 4a is the inside thread of connecting piece 312. Same components as in FIG. 4a are identified with the same reference numbers.

Figure 5A:
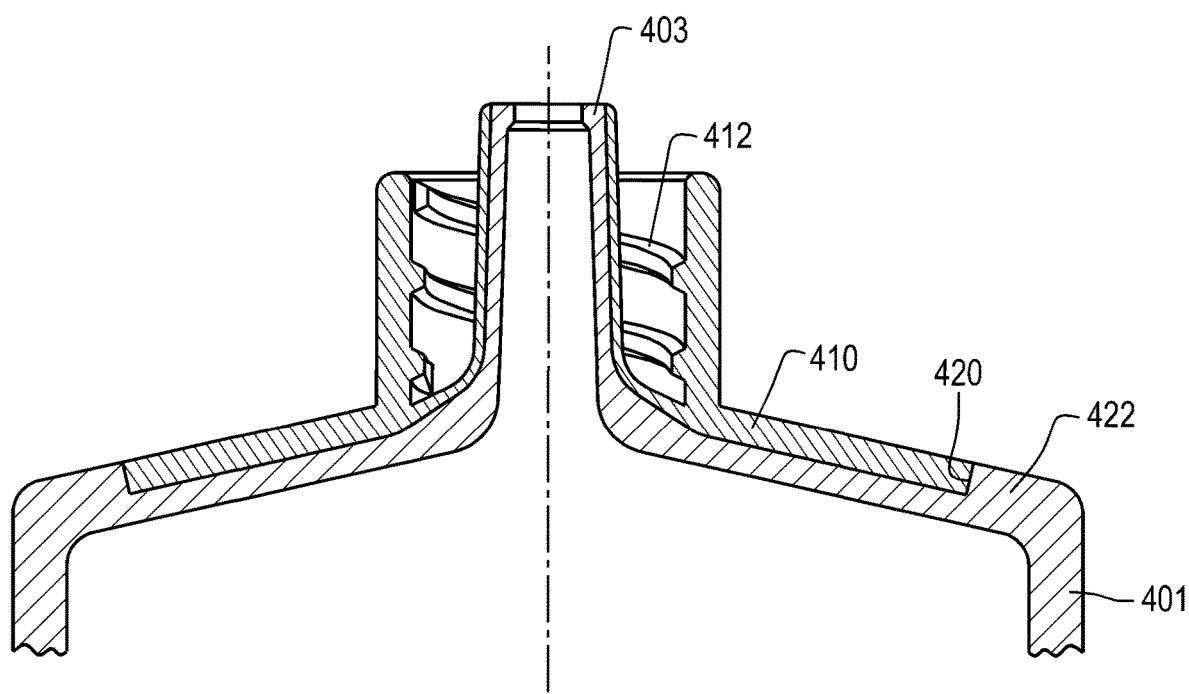
FIGS. 5a-5d is a second embodiment of a connector and syringe body created by means of multicomponent injection molding.
Figure 5B:
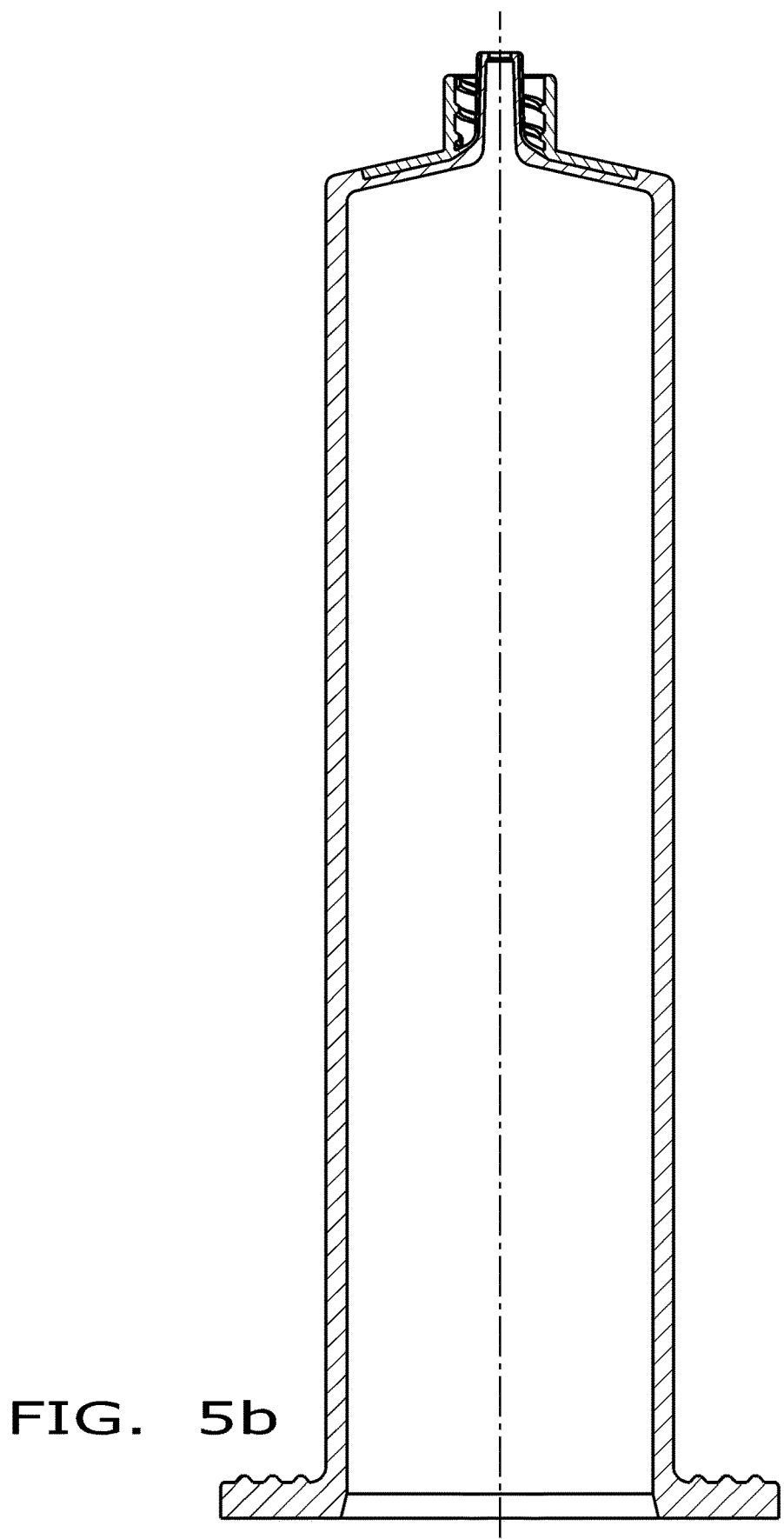
Figure 5C:
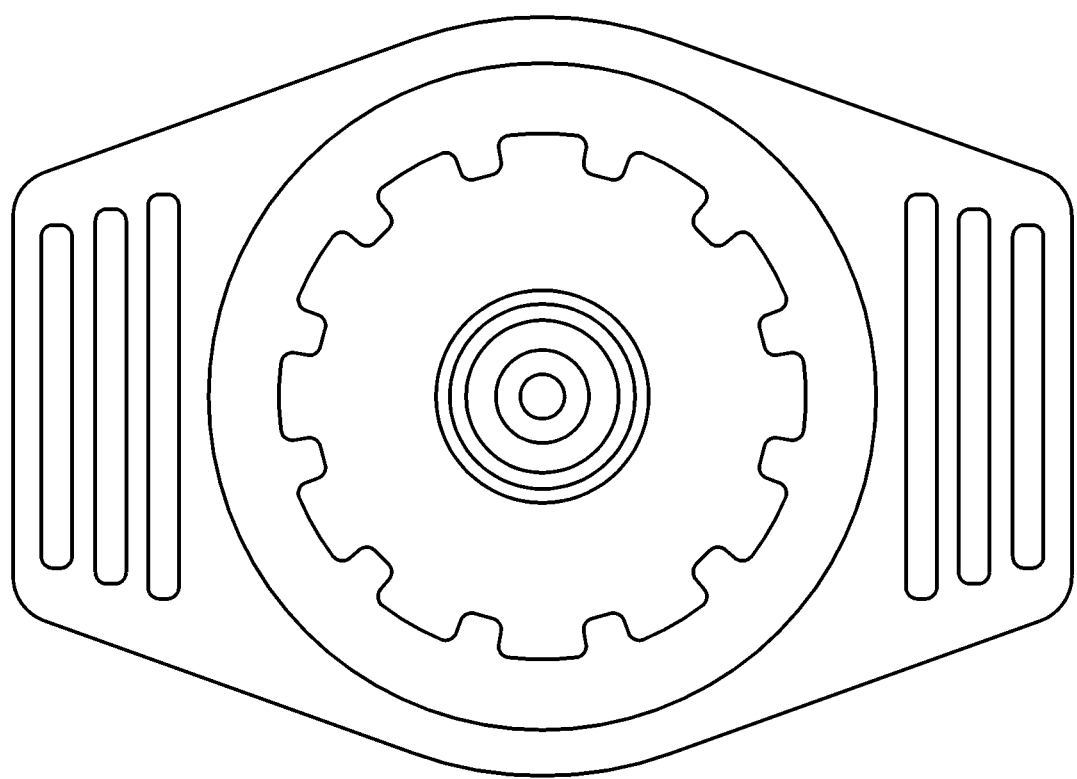
Figure 5D:
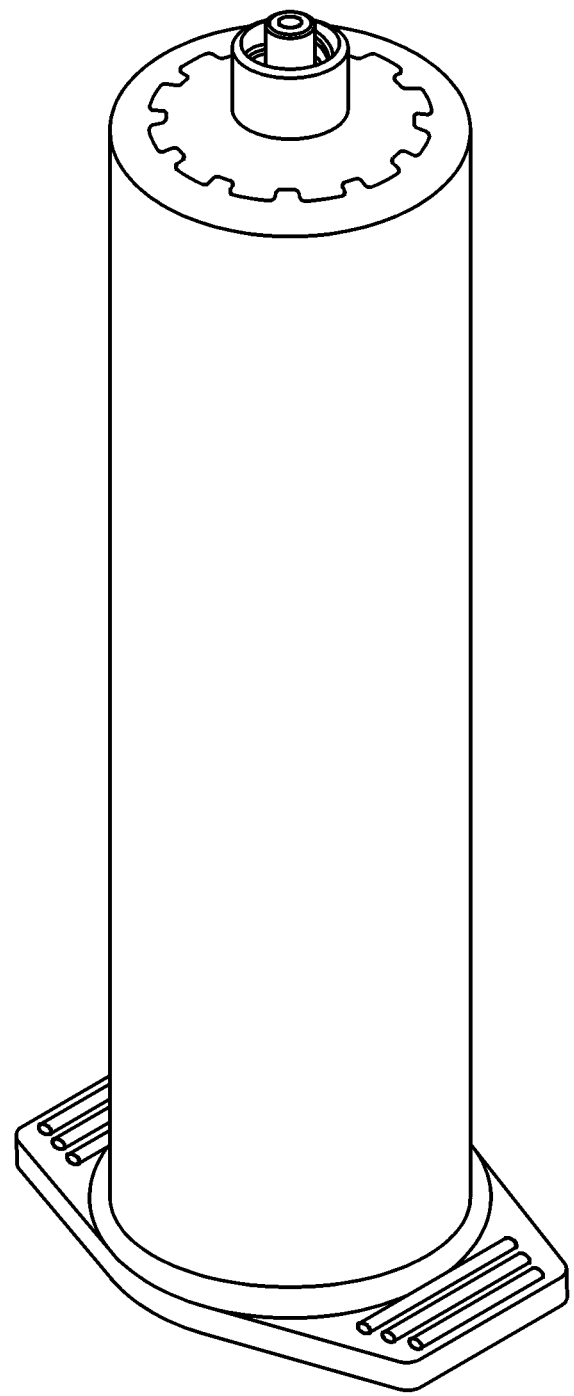

FIGS. 5a to 5d illustrate a second embodiment of a syringe body 401, produced by multicomponent injection molding. Connecting piece 410 in the region of syringe body 401 again consists of a softer material. The softer material has an E-module that is 10-60% lower than that of the hard material of the syringe body. It is typical for the second embodiment that syringe body 401 has a circumferential seating 420 in the region of cover 421 of the syringe body. The connecting piece consisting of a soft material engages into the seating. In the variation according to FIGS. 5a to 5d a larger contact surface is provided that permits improved adhesion of the materials with each other. This design also shows a connection of the softer material in the cone area, which effects development of the force peaks that occur there. The soft material of the connecting piece moreover surrounds also syringe cone 403 of tip 400 on outside 405. Clearly visible is also thread 412. FIG. 5b shows the entire syringe with connecting piece 410, FIG. 5c the top view and FIG. 5d a three-dimensional view. Same components as in FIG. 5a are identified with the same reference numbers.

In multicomponent injection molding the entire injection molded component is produced from two different plastics. For this purpose, the injection molding machine includes two injection units, whereby however only one clamping unit is required. The component that is produced in a multicomponent injection molding according to FIGS. 4a-5d can be produced cost effectively with only one tool in only one work cycle. In addition, geometries can be realized that would not be possible on an assembly.

The invention provides for the first time a syringe body with which it is possible to connect a multitude of different connectors with one connecting piece, wherein the insertion torque can fluctuate in a wide range, wherein the thread does not transfer the mechanical stress to the syringe body, which would result there in leaks.

Moreover, all materials of the syringe body as well as of the connecting piece are to be steam-sterilizable.

Moreover, the materials are selected so that they do not change when in contact with pharmaceutical media. Due to the softer material of the connecting piece, the coefficient of friction between the connector and the syringe is met, so that the thread cannot be over tightened.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method for producing a syringe including a syringe body having a first material and a connection having a second material that is softer than the first material, wherein the second material has an E-module that is 10 to 60% lower than the E-module of the first material, the method comprising:

producing the syringe through multicomponent injection molding, wherein the first material is a cycloolefin-copolymer (COC) or a cycloolefin-polymer (COP) and the second material comprises an elastomer.

2. The method according to claim 1, wherein the connection comprises a thread.

3. The method of claim 1, wherein the second material is sprayed onto the first material during the multicomponent injection molding.

4. The method of claim 1, wherein the second material surrounds a syringe cone of a tip of the produced syringe.

5. The method of claim 1, wherein the second material is a thermoplastic elastomer (TPE), an elastomer, a polypropylene (PP), a polycarbonate (PC), a polyethylene (PE), a polyamide (PA) or a COC-E.

6. The method of claim 1, wherein the second material has a higher coefficient of friction than the first material.

7. The method of claim 1, wherein the E-module of the first material is in the range of >2500 to 3500 MPa and the E-module of the second material in the range of 1200 to 2500 MPa.

8. The method of claim 1, wherein the E-module of the first material is in the range of 2700 to 3200 MPa and the E-module of the second material in the range of 1500 to 1800 MPa.

* * * * *